United States Patent [19]

Schally et al.

[11] Patent Number: 4,800,191

[45] Date of Patent: Jan. 24, 1989

[54] LHRH ANTAGONISTS

[76] Inventors: Andrew V. Schally, 5025 Kawanne Ave., Metarie, La. 70002; Sandor Bajusz, 10501 Curran Blvd. #5W, New Orleans, La. 70127

[21] Appl. No.: 74,126

[22] Filed: Jul. 17, 1987

[51] Int. Cl.$^4$ .................... A61K 37/43; C07K 7/20; C08F 283/00
[52] U.S. Cl. .................. 514/15; 525/54.11; 530/313; 514/800
[58] Field of Search ............ 530/313; 525/54.11; 514/15, 800

[56] References Cited

PUBLICATIONS

Chem. Abstr. vol. 82 (1975) 73465h.
Chem. Abstr. vol. 86 (1977) 5813c.

*Primary Examiner*—Delbert R. Phillips
*Attorney, Agent, or Firm*—Omri M. Behr

[57] ABSTRACT

The present invention deals with LHRH antagonists which possess improved water solubility and while having the high antagonist potency of the basic peptides, are free of the edematogenic effects. These compounds are highly potent in inhibiting the release of gonadotropins from the pituitary gland in mammals, including humans.

The compounds of this invention are represented by the formula $$X\text{-}R^1\text{-}R^2\text{-}R^3\text{-}Ser\text{-}Tyr\text{-}R^6\text{-}Leu\text{-}Arg\text{-}Pro\text{-}R^{10}\text{-}NH_2$$

wherein

X is an acyl group derived from straight or branched chain aliphatic or alicyclic carboxylic acids having from 1 to 7 carbon atoms, $R^1$ is D- or L-Pro, D- or L- $\Delta^3$-Pro, D-Phe, D-Phe(4-H1), D-Ser, D-Thr, D-Ala, D-Nal (1) or D-Nal (2), $R^2$ is D-Phe or D-Phe(4-H1)

$R^3$ is D-Trp, D-Phe, D-Pal, D-Nal(1) or D-Nal (2), $R^6$ is D-Cit, D-Hci, D-Cit(Q) or D-Hci(Q) and $R^{10}$ is Gly or D-Ala where Q is lower alkyl of 1–3 carbon atoms and H1 is fluoro, chloro or bromo, and the pharmaceutically acceptable acid addition salts thereof and methods of use pertaining to these compounds.

19 Claims, 1 Drawing Sheet

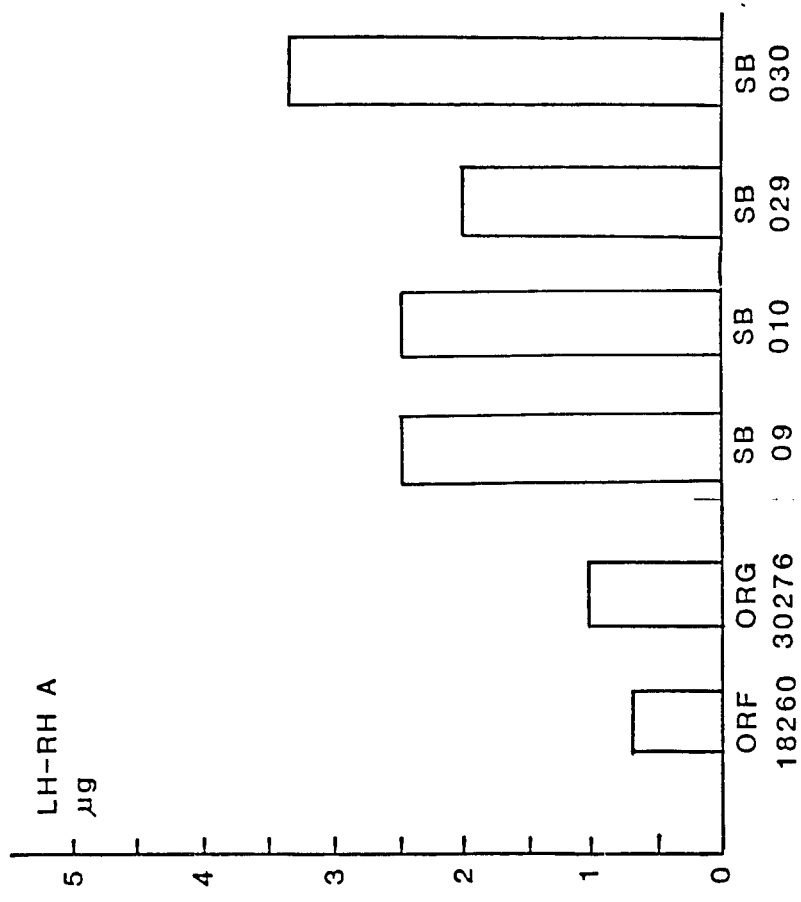

LHRH ANTAGONISTS

This invention was made with Government support under Grant Nos. CA40003 and 40004, awarded by the N.C.I. (NIH). The U.S. Government has certain rights in this application.

BACKGROUND OF THE INVENTION

The present invention relates to novel peptides which inhibit the release of gonadotropins by the pituitary gland in mammals without inducing edematous reactions. More specifically, the present invention relates to analogs of the luteinizing hormone releasing hormone (LHRH), which has the structure:

p-Glu-His-Trp-Ser-Tyr-Gly-Leu-Arg-Pro-Gly-NH$_2$, salts thereof, and to pharmaceutical compositions and methods of use pertaining to these analogs.

DISCUSSION OF THE PRIOR ART

For more than 15 years, investigators have been searching for selective, potent antagonists of the LHRH decapeptide (M. Karten and J. E. Rivier, Endocrine Reviews, 7, 44–66 (1986)). The high degree of interest in such antagonists is due to their usefulness in the fields of endocrinology, gynecology, contraception and cancer. A large number of compounds have been prepared as potential LHRH antagonists. The most interesting antagonists to date have been compounds whose structure is a modification of the structure of LHRH.

The first series of potent antagonists was obtained by introduction of aromatic acid residues into positions 1, 2, 3 and 6, or, 2, 3, and 6. The compounds are expressed as LHRH modified by replacement of the original amino acid residues by others at the position indicated by the superscript numbers. The known antagonists include:

[Ac-D-Phe(4-Cl)[1,2], D-Trp[3,6]] LHRH (D. H. Coy, et al., In: Gross, E. and Meienhofer, J. (eds) Peptides, Proceedings of the 6th. American Peptide Symposium, pp. 775–779, Pierce Chem. Co., Rockville, Il., 1979);

[Ac-Pro, D-Phe(4-Cl)[2] D-Nal(2)[3,6]]LHRH (U.S. Pat. No. 4,419,347); and

[Ac-ΔPro, D-Phe(4-Cl)[2], D-Trp[3,6]]LHRH (J. L. Pineda, et al., J. Clin. Endocrinol. Metab. 56, 420, 1983).

Later, in order to increase the water solubility of antagonists, basic amino acids, such as D-Arg, were introduced into position 6. For instance,

[Ac-D-Phe(4-Cl)[1,2], D-Trp[3], D-Arg[6], D-Ala[10]]LHRH (ORG-30276) (D. H. Coy, et al., Endocrinology, 100, 1445, 1982); and

[Ac-D-Nal(2)[1], D-Phe(4-F)[2], D-Trp[3], D-Arg[6]]LHRH (ORF-18260) (J. E. Rivier, et al., In: Vickery B. H., Nestor, Jr. J. J., Hafez, E. S. E. (eds), LHRH and Its Analogs, pp. 11–22, MTP Press, Lancaster, UK, 1984).

These analogs not only possessed the expected improved water solubility but also showed increased antagonistic activity. However, these highly potent, hydrophilic analogs containing D-Arg and other basic side chains at position 6 proved to produce transient edema of the face and extremities when administered subcutaneously in rats at 1.25 or 1.5 mg/kg (F. Schmidt, et al., Contraception, 29, 283, 1984; J. E. Morgan, et al., Int. Archs. Allergy Appl. Immun. 80, 70, (1986). Since the occurrence of edematogenic effects after administration of these antagonists to rats cast doubts on their safety for the use in humans and delayed the introduction of these drugs for clinical use, it is desirable to provide antagonistic peptides which are free of these side effects.

SUMMARY OF THE INVENTION

The present invention deals with LHRH antagonists which possess an improved water solubility and high antagonist potency of the basic peptides, and are free of the edematogenic effects. These compounds are highly potent in inhibiting the release of gonadotropins from the pituitary gland in mammals, including humans.

The compounds of this invention are represented by formula I $$X-R^1-R^2-R^3-Ser-Tyr-R^6-Leu-Arg-Pro-R^{10}-NH_2 \quad\quad I$$

wherein

X is an acyl group derived from straight or branched chain aliphatic or alicyclic carboxylic acids having from 1 to 7 carbon atoms, $R^1$ is D- or L-Pro, D- or L-$\Delta^3$-Pro, D-Phe, D-Phe(4-H1), D-Ser, D-Thr, D-Ala, D-Nal(1) or D-Nal (2), $R_3$ is D-Phe or D-Phe(4-H1)

$R_6$ is D-Trp, D-Phe, D-Pal, D-Nal(1) or D-Nal (2), $R_{10}$ is D-Cit, D-Hci, D-Cit(Q) or D-Hci(Q) and $R^{10}$ is Gly or D-Ala where Q is lower alkyl of 1–3 carbon atoms and H1 is fluoro, chloro or bromo, and the pharmaceutically acceptable acid addition salts thereof.

The compounds of Formula I can be prepared by several known techniques of the classical (solution) or solid phase peptide synthesis. Preferably, the compounds of Formula I are prepared from the analogous peptides of Formula II.

$$X_1-R^1-R^2-R^3-Ser(X^4)-Tyr(X^5)-R^{*6}(X^6)-Leu-Arg(X^8)-Pro-R^{10}-NH-X^{10} \quad\quad II$$

wherein $X_1$ is an acyl group derived from straight and branched chain aliphatic or alicyclic carboxylic acids having from 1 to 7 carbon atoms, t-Boc or hydrogen, $X^4$ is hydrogen or a protecting group for the Ser hydroxyl group, $X^5$ is hydrogen or a protecting group for the Tyr phenolic hydroxyl group, $X^8$ is hydrogen or a protecting group for the Arg guanidino group, $X^{10}$ is hydrogen or a resin support containing benzhydryl or methylbenzhydryl groups $R^1$ is D- or L-Pro, D- or L-$\Delta^3$-Pro, D-Phe, D-Phe(4-H1), D-Ser, D-Thr, D-Ala, D-Nal(1) or D-Nal(2), $R^2$ is D-Phe or D-Phe(4-H1), $^3$ is D-Trp, D-Phe, D-Pal, D-Nal(1) or D-Nal (2), $R^{*6}$ is D-Lys or D-Orn and $R^{10}$ is Gly or D-Ala where H1 is fluoro, chloro or bromo, provided that where $X_1$ is hydrogen or t-Boc, $X^4$, $X^5$, $X^6$, and $X^8$ must all be other than hydrogen.

The process comprises reacting a peptide of Formula II wherein $X^6$ is hydrogen, with a source of cyanate to yield a peptide of Formula III:

$$X_1-R^1-R^2-R^3-Ser(X^4)-Tyr(X^5)-R^{**6}-Leu-Arg(X^8)-Pro-R^{10}-NH-X^{10} \quad\quad III$$

wherein $X_1$, $R^1$, $R^2$, $R^3$, $X^4$, $X^5$, $X^8$, $R^{10}$ and $X^{10}$ are as defined above, and $R^{**6}$ is Cit or Hci. Suitably, the reaction is carried out when X is acyl and all other X moieties are hydrogen. Suitable cyanate sources are alkali metal cyanates, e.g., potassium cyanate, or an N-alkyl isocyanate, e.g., N-ethyl-isocyanate.

The peptide of Formula II are preferably synthesized by a known solid phase technique.

A gonadotropin antagonizing pharmaceutical composition is provided by admixing the compound of Formula I with a pharmaceutically acceptable carrier including microcapsules (microspheres) for delayed delivery.

There is also provided a method for relieving complications resulting from the physiological availability of amounts of pituitary gonadotropins in a mammal, in excess of the desired amount, which involves administering to the mammal a gonadotropin antagonizing dose of the compound of Formula I.

DESCRIPTION OF THE DRAWINGS

FIG. 1 is a bar graph of certain compounds of this invention and prior art compounds showing concentration required to induce relaese of 50% of rat peritoneal mast cell histamine.

DESCRIPTION OF THE PREFERRED EMBODIMENTS

The nomenclature used to define the peptides is that specified by the IUPAC-IUB Commission on Biochemical Nomenclature (*European J. Biochem.*, 1984, 138, 9–37), wherein in accordance with conventional representation the amino groups at the N-terminus appears to the left and the carboxyl group at the C-terminus to the right. By natural amino acid is meant one of the common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. The abbreviations for the individual amino acid residues are based on the trivial name of the amino acid and are Ala, alanine; Arg, arginine, Cit, citrulline, Gly, glycine; Hci, homocitrulline; Leu, leucine; Lys, lysine; Pal, 3-(3-pyridyl) alanine; Nal(2), 3-(2-naphthyl)alanine; Orn, ornithine; Phe, phenylalanine; Phe(4-Cl), 4-chlorophenylalanine; Phe (4-F), 4-fluorophenylalanine; Pro, proline; Ser, serine; Trp, tryptophan and Tyr, tyrosine. All amino acids described herein are of the L-series unless stated otherwise, e.g., D-Trp represents D-tryptophan and D-Nal (2) represents 3-(2-naphthyl)-D-alanine.

Other abbreviations used are:

AcOH: acetic acid
AcOEt: ethyl acetate
Ac$_2$O: acetic anhydride
Boc-: tert.butyloxycarbonyl-
DIC: diisopropylcarbodiimide
DIEA: diisopropylethylamine
DMF: dimethylformamide
HOBt: 1-hydroxybenzenetriazole hydrate
HPLC: high performance liquid chromatography
MeOH: methyl alcohol
TEA: triethylamine
DCC: dicyclohexylcarbodiimide
MeCN: acetonitrile
IpOH: isopropanol
Z(2-Cl): 2-chloro-benzyloxycarbonyl
DCB: 2,6-dichlorobenzyl
Tos: p-toluenesulfonyl
TFA: trifluoroacetic acid
Z: benzyloxycarbonyl Especially preferred are LHRH analogs of Formula I wherein:

X is acetyl
$R_2$ is Pro, D-Phe, D-Phe(4-Cl) or D-Nal(2),
$R_3$ is D-Phe(4-Cl) or D-Phe(4-F),
$R_6$ is D-Trp.
$R_{10}$ is D-Cit, D-Hci, D-Cit(Et) or D-Hci(Et) and
$R^{10}$ is D-Ala.

The peptides are synthesized by a suitable method, such as by exclusively solid-phase techniques, by partial solid-phase techniques, by fragment condensation or by classical solution phase synthesis. (See M. Bodanszky, "Principles of Peptide Synthesis", Springer-Verlag, 1984).

For example, the techniques of exclusively solid-phase synthesis are set forth in the textbook "Solid Phase Peptide Synthesis", J. M. Stewart and J. D. Young, Pierce Chem. Company, Rockford, Ill., 1984 (2nd. ed.), G. Barany and R. B. Merrifield, "The Peptides", Ch. 1, 1–285, pp. 1979, Academic Press, Inc.

Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Germany.

Common to such synthesis is the protection of the reactive side chain functional groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting groups to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

The procedures of the present invention may be carried out using a variety of support phases. These support phases may be for example, resins such as benzhydrylamine resins (suitably 2% cross linked), p-methylbenzhydrylamine resins (suitably 2% cross linked) and the like.

In Formula II:

$R^1$, $R^2$, and $R^3$ are as defined hereinabove,
$X_1$ is hydrogen or an acyl group derived from straight or branched chain aliphatic or alicyclic carboxylic acids having from 1 to 7 carbon atoms, or an alpha-amino protecting group. The alpha-amino protecting groups contemplated by $X^1$ are those well known to be useful in the art of step-wise synthesis of polypeptides. Among the classes of alpha-amino protecting groups which may be employed as $X^1$ may be mentioned fluoroenylmethyloxycarbonyl (Fmoc) or t-butyloxycarbonyl (Boc).

$X^4$ may be a suitable protecting group for the hydroxyl group of Ser such as benzyl (Bzl), and 2,6-dichlorobenzyl (DCB). The preferred protecting group is Bzl.

$X^5$ may be a suitable protecting group for the phenolic hydroxyl group of Tyr, such as Bzl, 2-Br-Z and 2,6- dichloro-benzyl (DCB). The preferred protecting group is DCB.

$X^6$ is a suitable protecting group for the side chain amino group of Lys or Orn. Illustrative of suitable side chain amino protecting groups are benzyloxycarbonyl (Z), and 2-chloro-benzyloxycarbonyl (Z-(2-Cl).

$X^8$ is a suitable protecting group for the guanidino group of Arg, such as nitro, Tos, methyl-(t-butyl benzene)-sulfonyl, 4-methoxy-2,3,6-trimethylbenzenesulfonyl; Tos is the preferred group.

Provided that where X is hydrogen or t-Boc, $X^4$, $X^5$, $X^6$ and $X^8$ are other than hydrogen.

The selection of a side chain amino protecting group is not critical except that generally one is chosen which is not removed during deprotection of the alpha-amino groups during the synthesis.

For intermediates A, the values for $X^4$, $X^5$, $X^6$, $X^8$ and $X^{10}$ are hydrogen, for intermediates B, the values for $X^4$, $X^5$, $X^6$, $X^8$, and $X^{10}$ are protecting groups.

The peptides of Formula I are preferably prepared from intermediates A which are obtained from intermediates B by procedures known in the art.

Intermediates B are preferably prepared by a solid-phase synthesis, such as described by Merrifield, J. Am. Chem. Soc., 85, p. 2149 (1963). Solid phase synthesis is commenced from the C-terminal end of the peptide by coupling a protected α-amino acid to a suitable resin. Such a starting material can be prepared by attaching α-amino protected Gly or D-Ala by an amide bond to a benzyhydrylamine resin. Such resin supports are commercially available and generally used when the desired polypeptide being synthesized has an α-carboxamide at the C-terminal.

In one embodiment of the synthesis, the primary amino group of Gly or D-Ala is protected with a t-butoxy carbonylating agent and the coupling carried out using any of the known dialkyl carbodiimide coupling procedures.

The selection of an appropriate coupling reagent is within the skill of the art. Particularly suitable as a coupling reagent is N,N'-diisopropyl carbodiimide (DIC).

Activating reagents and their use in peptide coupling are described by M. Bodanszky, "Principles of Peptide Synthesis", Springer-Verlag, 1984.

Each protected amino acid or amino acid sequence is introduced into the solid phase reactor in about a twofold excess, and the coupling may be carried out in a medium of DMF:$CH_2Cl_2$ (1:1) or in $CH_2Cl_2$ alone. In cases where incomplete coupling occurs, the coupling procedure is repeated before removal of the alpha-amino protecting group prior to the coupling of the next amino acid. The success of the coupling reaction at each stage of the synthesis, is preferably monitored by the ninhydrin reaction, as described by E. Kaiser, et al., Anal. Biochem., 34, 595 (1970).

After the desired amino acid sequence of intermediates B has been completed. The terminal Boc group is removed and N-terminal acylation carried out using the appropriate acyl anhydride or acid chloride in 50-fold excess in a halogenated hydrocarbon solvent; suitably, acetic anhydride in methylene chloride for 30 minutes. The intermediate peptide can be removed from the resin support by treatment with a reagent such as liquid hydrogen fluoride, which not only cleaves the peptide from the resin but also cleaves all remaining side chain protecting groups $X^4$, $X^5$, $X^6$, $X^8$, and $X^{10}$.

When using hydrogen fluoride for cleaving, anisole and, if desired, methylethyl sulfide are included as scavengers in the reaction vessel, to yield Intermediates A.

Intermediates A are converted into peptides of Formula I by treatment with cyanate, suitably an alkali metal cyanate, preferably potassium cyanate, or an N-alkylisocyanate, for instance, N-ethylisocyanate, in DMF or aqueous DMF. The latter reaction, i.e., transformation of Orn/Lys-peptides into the corresponding Cit/Hci-peptides can be readily followed by HPLC using MeCN-aqueous TFA systems because of a characteristic 2.6±0.3 minutes increase of the retention times of Cit/Hci—and, for example, Cit (Et)/Hci(Et)-peptides relative to the corresponding Orn/Lys-peptides respectively.

Although a partial solid-phase synthesis of compounds of Formula I is disclosed herein, the preparation of the compounds also can be realized by exclusively solid-phase synthesis or by classical solution-phase methods.

The synthetic peptides prepared as described in the Examples are compared with two of the most potent LHRH antagonists reported recently, i.e., [Ac-D-Phe(4-Cl)[1,2], D-Trp[3], D-Arg[6], D-Ala[10]] LHRH (ORG-30276) (Coy, et al., Endocrinology, 100, 1445, 1982) and [Ac-D-Nal(2), D-Phe(4-F)[2], D-Trp[3], D-Arg[6]] LHRH (ORF 18260) (Rivier, et al., In: Vickery, B. H., Nestor, Jr., J. J. Hafez, E. S. E. (eds.), LHRH and Its Analogs, pp. 11–22, MPT Press, Lancaster, UK, 1984), and are found to exert similarly high inhibitory activities both in vitro and in vivo, but, unlike to the control peptides, not to produce the in vivo edematous effects.

Hormonal activities in vitro are compared in superfused rat pituitary cell systems (S. Vigh and A. V. Schally, Peptides. 5 suppl. 1: 241–247, 1984) in which the effectiveness of LHRH (and other releasing hormones) can be accurately evaluated since the amount of LH (or other pituitary hormones) secreted into the effluent medium is not only proportional to the hormone-releasing potency of the peptide applied but also measurable readily by well-characterized radioimmunoassays.

To determine the potency of an LHRH antagonist, mixtures containing LHRH in a constant concentration (usually 1 nM) and the antagonist in varying concentrations are used for the superfusion in order to determine the molecular ratio of the antagonist to LHRH at which the action of LHRH is completely blocked. These ratios are about 5 for both peptides of the present invention and the control peptides when the rat pituitary cell system is preincubated with antagonists for 9 minutes.

In an antiovulatory in vivo assay (A. Corbin and C. W. Beattie; Endocr. Res. Commun. 2, 1–23, 1975; D. H. Coy, et al., Endrocrinology, 100, 1445, 1982), the peptides of the present invention are also found to be about equipotent to the control antagonist, namely, 87.5–100% blockage of ovulation can be observed at a subcutaneous dose of 1–3 ug/rat for each peptide.

In the edematogenic test of Schmidt, et al. (Contraception, 29, 283–289, 1984), however, a marked difference can be found between the control peptides and the peptides of the present invention. The control peptides produce edema of the face and extremities when administered subcutaneously in rats at doses of 0.75 or 1.25 mg/kg. No such reaction can be observed with the peptides of the present invention when given at a subcutaneous dose of 1.5 mg/kg.

In the tests as run the rats were assigned to three groups of five rats per group per compound tested. Comparison with made with a known prior art compound designated ORG 30276 namely (N-Ac-D-p-Cl-Phe[1,2], D-Trp[3], D-Arg[6], D-Ala[10])-LHRH. The groups were injected subcuntaneously once a day on two consecutive days with the LHRH antagonists at a dose level of 1.5 mg/kg. One control group was injected with diluent only. The rats were observed during five hours each day. Reactions of the rats were classified as follows: NR no apparent reaction, PR partial responders: edema of the nasal and paranasal area, FR full responders: facial edema with edematous extremities. These results are summarized in Table 1 below.

TABLE 1

| LHRH Antagonist | 1st Day | | | 2nd Day | | |
|---|---|---|---|---|---|---|
| | NR | PR | FR | NR | PR | FR |
| ORG 30276 | 4 | 5 | 0 | 1 | 2 | 6 |
| ORG 30276 | 1 | 3 | 0 | 0 | 1 | 3 |
| Control | 9 | 0 | 0 | 9 | 0 | 0 |
| EX III | 8 | 0 | 0 | | | |
| EX V | 9 | 0 | 0 | 8 | 1* | 0 |
| EX IV | 9 | 0 | 0 | 9 | 0 | 0 |
| EX I | 8 | 0 | 0 | 8 | 0 | 0 |

All peptides shown are completely effective to block LHRH secretion in vitro at some reasonable concentration, altough most are slightly less potent than the present standard in vitro; however, these peptides are much more potent in vivo.

This was shown by a test on histamine release in vitro from peritoneal mast cells carried out in accordance with the procedure of Morgan et al (Int. Archs. Allergy appl. Immun. 80, 70 1986).

HISTAMINE RELEASE IN VITRO

In this test rats were anesthetized with ether and peritoneal exudate cell were harvested by washing with 12 ml. of mast cell medium (MCM) (150 m M NaCl; 3.7 m M KCl; 3.0 m M Na$_2$HPO$_4$; 3.5 m M KH$_2$PO$_4$, 0.98 m M CaCl; 5.6 m M dextrose; 0.1% bovine serum albumin; 0.1% gelatin and 10 units/ml heparin) [9]. Cells from 4 or 5 rats were pooled, centrifuged at 120 g, resuspended with MCM to a concentration of $0.5 \times 10^6$ ml and 1 ml was aliquoted into 12×75 mm polyethylene tubes. Tubes were equilibrated to 37° C. for 15 min and incubated alone (background histamine release), with 48/80 (positive control) (Sigma Chemicals, St. Louis, Mo.), or with appropriate concentrations (1 ng through 10 ug/ml) of LHRH antagonists for 60 min. The reaction was terminated by cooling the tubes to 4° C. Tubes were centrifuged; supernatants were recovered and stored at −20° C. until assayed for histamine. Assays were performed in duplicate. Total cell histamine was determined by boiling for 10 min. Histamine released in reponse to antagonist was expressed as a percentage of total release. That concentration that released 50% of total mast cell histamine (HRD$_{50}$ ug/ml) was determined for each antagonist. The results are summarized in FIG. 1

All of the peptides are considered to be effective to prevent ovulation of female mammals at very low dosages. The peptides of the invention are often administered in the form of pharmaceutically acceptable, non-toxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like. If the active ingredient is to be administered in tablet form, the tablet may contain a pharmaceutically acceptable diluent which includes a binder, such as tragacanth, corn starch or gelatin; a disintegrating agent, such as alginic acid and a lubricant, such as magnesium stearate.

If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given introvenously; oral dosages will be higher. Overall, treatment of subjects with these peptides is generally carried out in the same manner as the clinical treatment using other antagonists of LHRH.

These peptides can be administered to mammals intravenously, subcutaneously, intramuscularly, orally, intranasally or intravaginally to achieve fertility inhibition and/or control and also in applications calling for reversible suppression of gonadal activity, such as for the management of precocious puberty or during radiation- or chemo-therapy. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications obvious to one having the ordinary skill in his art may be made without departing from the scope of the invention, which is set forth in the claims which are appended thereto. Substitutions known in the art which do not significantly detract from its effectiveness may be employed in the invention.

EXAMPLE I

The synthesis of an analog of the formula:

Ac-D-Nal(2)-D-Phe(4-Cl)-D-Trp-Ser-Tyr-D-Hci-Arg-Pro-D-Ala-NH$_2$ was commenced with the preparation of the intermediate peptide Ac-D-Nal(2)-D-Phe(4-Cl)-D-Trp-Ser-Tyr-Lys-Leu-Arg-Pro-D-AlaNH$_2$. The intermediate peptide was built step by step on a benzhydrylamine resin containing about 0.6 m.equiv. NH$_2$/g (from BACHEM) on a Beckman 990 synthesizer starting with the Boc-Gly in accordance with the procedures set forth below.

Coupling is carried out in accordance with Schedule A as follows:

SCHEDULE A

| Reagent | Mixing Time (mins) |
|---|---|
| 1. Boc Amino Acid (0.9-1.2 m mole/g. resin) + equiv amt. of DIC | 60-90 |
| 2. MeOH (twice) | 1 |

-continued

SCHEDULE A

| Reagent | Mixing Time (mins) |
|---|---|
| 3. $CH_2Cl_2$ (twice) | 1 |

Deblocking is carried out in accordance with Schedule B as follows:

SCHEDULE B

| Reagent | Mixing Time (mins) |
|---|---|
| 4. 50% TFA/1% ethanedithiol in $CH_2Cl_2$ (x2) | 15 & 15 |
| 5. IpOH/1% ethane dithiol | 1 |
| 4. 10% TEA in $CH_2Cl_2$ | 2 |
| 7. MeOH | 1 |
| 8. 10% TEA in $CH_2Cl_2$ | 2 |
| 9. MeOH (x2) | 1 & 1 |
| 10. $CH_2Cl_2$ (x2) | 1 & 1 |

The phenolic hydroxyl group of Tyr is protected with 2,6-dichlorobenzyl (DCB).

Briefly, Boc is used for N-terminal protection. Tos is used to protect the guanidino group of Arg. Z(2-Cl) is used as the protecting group for the D-Lys side chain, Bzl for the OH group of Ser and Tyr is protected with DCB.

One and a half to two-fold excess of protected amino acid is used based on the $NH_2$-content of the benzhydrylamine-resin, plus one equivalent of DIC in $CH_2Cl_2$ or 10–50% DMF/$CH_2Cl_2$, depending on the solubility of Boc-amino acid, for two hours.

N-Terminal acetylation is performed with a 50-fold excess of acetic anhydride in $CH_2Cl_2$ for 0.5 hours. The protected intermediate peptide thus obtained has the following composition: Ac-D-Nal(2)-D-Phe(4-Cl)-D-Trp-Ser($X^4$)-Tyr-($X^5$)D-Lys($X^6$)-Leu-Arg($X^8$)-Pro-D-Ala-NH-$X^{10}$ wherein $X^4$ is Bzl and $X^5$ is DCB, $X^6$ is Z(2-Cl), $X^8$ is Tos, and $X^{10}$ is a benzhydryl group incorporated into the resin.

In order to cleave and deprotect the protected peptide-resin, it is treated with 1.4 ml. m-cresole and 15 ml. hydrogen fluoride per gram of peptide-resin for 0.5 hours at 0° and 0.5 hours at room temperature. After elimination of hydrogen fluoride under high vacuum, the resin-peptide is washed with diethyl ether and the peptide is then extracted with DMF and separated from the resin by filtration. The DMF solution is concentrated to a small volume under high vacuum, then triturated with diethyl ether. The crude product thus obtained is purified by preparative HPLC as described below, to give the pure free intermediate peptide having the above-mentioned structure wherein $X^4$, $X^5$, $X^6$, $X^8$ and $X^{10}$ are hydrogen.

The free D-Lys$^6$-containing intermediate peptide is then reacted with potassium cyanate in 80% aqueous DMF solution (81 mg. KCNO/ml) at ambient temperature for 24 hours. The reaction mixture, after evaporation under high vacuum, is subjected to purification by preparative HPLC to yield the desired D-Hci-containing peptide. The peptide is judged to be substantially (95%) pure by using HPLC. HPLC analyses are carried out in a Hewlett-Packard 1090A gradient liquid chromatographic system on a C18 column (VYDAC 218TP546) eluted with solvents A: 0.1% TFA, B: 0.1% TFA in 70% $CH_3CN$ with a gradient of 30–60% in 30 minutes. The intermediate peptide and the desired peptide have retention times of 25.5 minutes and 28.2 minutes, respectively.

Purification of peptides is carried out on a Beckman Prep-350 gradient liquid chromatograph using a 41.4×250 mm preparative reversed phase DYNEMAX C18 cartridge (300A, 12 um) with solvents A: 0.1% TFA and B: 0.1% TFA in 70% $CH_3CN$ and using a gradient of 45–60% in 30 minutes.

EXAMPLE II

The synthesis of the peptide Ac-D-Nal(2)-D-Phe(4-Cl)-D-Trp-Ser-Tyr-D-Hci(Et)-Leu-Arg-Pro-D-Ala-$NH_2$ is accomplished by reacting the intermediate peptide Ac-D-Nal(2)-Phe(4-Cl)-D-Trp-Ser-Tyr-D-Lys-Leu-Arg-Pro-D-Ala-$NH_2$ described in Example I, with N-ethylisocyanate in DMF (0.1 mg. in 0.01 ml. per gm of intermediate) at 0°–10° for 10 hours. Retention time for the desired peptide is 30.8 min.

EXAMPLE III

The synthesis of the peptide Ac-D-Nal(2)-D-Phe(4-Cl)-D-Trp-Ser-Tyr-D-Cit-Leu-Arg-Pro-D-Ala-$NH^2$ is conducted as described in Example I with the exception that Boc-D-Orn(Z) is incorporated in place of Boc-D-Lys[Z-(2-Cl)] in position 6 of the intermediate peptide to afford another intermediate peptide having the formula Ac-D-Nal(2)-D-Phe (4-Cl)-D-Trp-Ser-Tyr-D-Orn-Leu-Arg-Pro-D-Ala-$NH_2$, which is then similarly converted to the desired peptide. This intermediate peptide and the desired peptide have HPLC retention times of 25.5 min. and 27.8 min., respectively.

EXAMPLE IV

The synthesis of the peptide Ac-D-Nal(2)-D-Phe(4-Cl)-D-Trp-Ser-Tyr-D-Cit(Et)-Leu-Arg-Pro-D-Ala-$NH_2$ is accomplished by reacting the intermediate peptide Ac-D-Nal(2)-Phe(4-Cl)-D-Trp-Ser-Tyr-D-Orn-Leu-Arg-Pro-D-Ala-$NH_2$ described in Example III, with N-ethylisocyanate in DMF (0.1 mg. in 0.01 ml. per gm of intermediate) at 0°–10° for 10 hours. Retention time for the desired peptide is min.

EXAMPLE V

The synthesis of the peptide Ac-D-Phe(4-Cl)-D-Phe(4-Cl)-D-Trp-Ser-Tyr-D-Hci-Leu-Arg-Pro-D-Ala-$NH_2$ is conducted as described in Example I, with the exception that Boc-D-Phe(4-Cl) is incorporated in place of Boc-D-Nal(2) in position 1 of the intermediate peptide to give another intermediate peptide having the formula Ac-D-Phe(4-Cl)-D-Phe(4-Cl)-D-Trp-Ser-Tyr-D-Lys-Leu-Arg-Pro-D-Ala-$NH_2$, which is then similarly converted to the desired peptide. This intermediate peptide and the desired peptide have retention times of 24.0 min. and 26.6 min., respectively.

EXAMPLE VI

The synthesis of the peptide Ac-D-Phe(4-Cl)-D-Phe(4-Cl)-D-Trp-Ser-Tyr-D-Hci(Et)-Leu-Arg-Pro-D-Ala-$NH_2$ is accomplished by reacting the intermediate peptide Ac-D-Phe(4-Cl)-Phe(4-Cl)-D-Trp-Ser-Tyr-D-Lys-Leu-Arg-Pro-D-Ala-$NH_2$ described in Example V with N-ethylisocyanate in DMF (0.1 mg. in 0.01 ml. per gm of intermediate) at 0°–10° for 10 hours. Retention time for the desired peptide is 29.2 min.

EXAMPLE VII

The synthesis of the peptide Ac-D-Phe(4-Cl)-D-Phe(4-Cl)-D-Trp-Ser-Tyr-D-Cit-Leu-Arg-Pro-D-Ala- NH₂ is conducted as described in Example I, with the exception that Boc-D-Phe(4-Cl) is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-D-Phe(4-Cl)-D-Phe(4-Cl)-D-Trp-Ser-Tyr-D-Orn-Leu-Arg-Pro-D-Ala-NH₂, which is then similarly converted to the desired peptide. This intermediate peptide and the desired peptide have retention times of 24.0 min. and 26.3 min., respectively.

EXAMPLE VIII

The synthesis of the peptide Ac-D-Phe(4-Cl)-D-Phe(4-Cl)-D-Trp-Ser-Tyr-D-Cit(Et)-Leu-Arg-Pro-D-Ala-NH₂ is accomplished by reacting the intermediate peptide Ac-D-Phe(4-Cl)-D-Phe(4-Cl)-D-Trp-Ser-Tyr-D-Orn-Leu-Arg-Pro-D-Ala-NH₂ described in Example VII, with N-ethylisocyanate in DMF (0.1 mg. in 0.01 ml. per gm of intermediate) at 0°–10° for 10 hours. Retention time for the desired peptide is 28.6 min.

EXAMPLE IX

The synthesis of the peptide Ac-D-Nal(2)-D-Phe(4-Cl)-D-Trp-Ser-Tyr-D-Hci-Leu-Arg-Pro-Gly-NH₂ is conducted as described in Example I to afford another intermediate peptide having the formula Ac-D-Nal(2)-D-Phe(4-Cl)-D-Trp-Ser-Tyr-D-Lys-Leu-Arg-Pro-Gly-NH₂, which is then similarly converted to the desired peptide. This intermediate peptide and the desired peptide have HPLC retention times of 24.8 min. and 27.4 min., respectively.

EXAMPLE X

The synthesis of the peptide Ac-D-Nal(2)-D-Phe(4-Cl)-D-Trp-Ser-Tyr-D-Hci(Et)-Leu-Arg-Pro-Gly-NH₂ is accomplished by reacting the intermediate peptide Ac-D-Nal(2)-Phe(4-Cl)-D-Trp-Ser-Tyr-D-Lys-Leu-Arg-Pro-Gly-NH₂ described in Example IX with N-ethylisocyanate in DMF 0.1 mg. in 0.01 ml. per gm of intermediate) at 0°–10° for 10 hours. Retention time for the desired peptide is 30.0 min.

EXAMPLE XI

The synthesis of the peptide Ac-Pro-D-Phe(4-Cl)-D-Trp-Ser-Tyr-D-Hci-Leu-Arg-Pro-D-Ala-NH₂ is conducted as described in Example I with the exception that Boc-Pro is incorporated in place of Boc-D-Nal(2) in position 1 of the intermediate peptide to afford another intermediate peptide having the formula Ac-Pro-D-Phe(4-Cl)-D-Trp-Ser-Tyr-D-Lys-Leu-Arg-Pro-D-Ala-NH₂, which is then similarly converted to the desired peptide. This intermediate peptide and the desired peptide have retention times of 16.8 min. and 19.3 min., respectively.

EXAMPLE XII

The synthesis of the peptide Ac-Pro-D-Phe(4-Cl)-D-Trp-Ser-Tyr-D-Hci(Et)-Leu-Arg-Pro-D-Ala-NH₂ is accomplished by reacting the intermediate peptide Ac-D-Pro-Phe(4-Cl)-D-Trp-Ser-Tyr-D-Lys-Leu-Arg-Pro-D-Ala-NH₂ described in Example XI, with N-ethylisocyanate in DMF (0.1 mg. in 0.01 ml. per gm of intermediate) at 0°–10° for 10 hours. Retention time for the desired peptide is 22.0 min.

EXAMPLE XIII

The synthesis of the peptide Ac-Pro-D-Phe(4-Cl)-D-Trp-Ser-Tyr-D-Cit-Leu-Arg-Pro-D-Ala-NH₂ is conducted as described in Example I, with the exception that Boc-Pro is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-Pro-D-Phe(4-Cl)-D-Trp-Ser-Tyr-D-Orn-Leu-Arg-Pro-D-Ala-NH₂. This intermediate peptide and the desired peptide have retention times of 16.85 min. and 18.8 min., respectively.

EXAMPLE XIV

The synthesis of the peptide Ac-Pro-D-Phe(4-Cl)-D-Trp-Ser-Tyr-D-Cit(Et)-Leu-Arg-Pro-D-Ala-NH₂ is conducted as described in Example VI, with the exception that the intermediate peptide Ac-Pro-D-Phe(4-Cl)-D-Trp-Ser-Tyr-D-Orn-Leu-Arg-Pro-D-Ala-NH₂ described in Example XIII is reacted with N-ethylisocyanate. The desired peptide has a retention time of 24.9 min.

EXAMPLE XV

The synthesis of the peptide Ac-D-Phe-D-Phe(4-Cl)-D-Trp-Ser-Tyr-Hci-Leu-Arg-Pro-D-Ala-NH₂ is conducted as described in Example I, with the exception that Boc-D-Phe is incorporated in place of Boc-D-Nal(2) in position 1 of the intermediate peptide to yield another intermediate peptide having the formula Ac-D-Phe(4-Cl)-D-Trp-Ser-Tyr-D-Lys-Leu-Arg-Pro-D-Ala-NH₂, which is then similarly converted to the desired peptide. This intermediate peptide and the desired peptide have HPLC retention times of 20.8 min. and 23.4 min., respectively.

EXAMPLE XVI

The synthesis of the peptide Ac-D-Phe-D-Phe(4-Cl)-D-Trp-Ser-Tyr-D-Hci(Et)-Leu-Arg-Pro-D-Ala-NH₂ is accomplished by reacting the intermediate peptide Ac-D-Phe-D-Phe(4-Cl)-D-Trp-Ser-Tyr-D-Lys-Leu-Arg-Pro-D-Ala-NH₂ described in Example XV, with N-ethylisocyanate in DMF (0.1 mg. in 0.01 ml. per gm of intermediate) at 0°–10° for 10 hours. Retention time for the desired peptide is 26.0 min.

EXAMPLE XVII

The synthesis of the peptide Ac-D-Phe-D-Phe(4-Cl)-D-Trp-Ser-Tyr-D-Cit-Leu-Arg-Pro-D-Ala-NH₂ is conducted as described in Example I, with the exception that Boc-D-Phe is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-D-Phe-D-Phe(4-Cl)-D-Trp-Ser-Tyr-D-Orn-Leu-Arg-Pro-D-Ala-NH₂. This intermediate peptide and the desired peptide have retention times of 21.0 min. and 23.1 min., respectively.

EXAMPLE XVIII

The synthesis of the peptide Ac-D-Phe-D-Phe(4-Cl)-D-Trp-Ser-Tyr-D-Cit(Et)-Leu-Arg-Pro-D-Ala-NH₂ is accomplished by reacting the intermediate peptide Ac-D-Phe-D-Phe(4-Cl)-D-Trp-Ser-Tyr-D-Orn-Leu-Arg-Pro-D-Ala-NH₂ described in Example XVII, with N-ethylisocyanate in DMF (0.1 mg. in 0.01 ml. per gm of intermediate) at 0°–10° for 10 hours. Retention time for the desired peptide is 25.4 min.

Similarly, there may be prepared the acid addition salts of the other peptides analogous to LHRH, described herein.

EXAMPLE XIX

A solution of 0.1 g. of the hydrogen fluoride salt of Ac-D-Nal(2)-D-Phe(4-Cl)-D-Trp-Ser-Tyr-D-Hci-Leu-Arg-Pro-D-Ala-$NH_2$ (See Example I) is dissolved in 5 ml of water and passed through a column of 5 g. Dowex 3 anion exchange resin which had previously been equilibrated with acetic acid and washed with deionized water and the effluent is lyophilized to yield the corresponding acetic acid salt of Ac-D-Nal(2)-D-Phe(4-Cl)-D-Trp-Ser-Tyr-D-Hci-Leu-Arg-Pro-D-Ala-$NH_2$.

Repeating the above, substituting other acids of acetic acid during the equilibration of the resin, there may be obtained, for example, the corresponding salts with hydrochloric acid, hydrobromic acid, sulfuric acid, phosphoric acid, benzoic acid, and the like.

EXAMPLE XX

Tablet formulation for buccal (e.g., sublingual) administration:
1. LHRH Antagonist 10.0 mg.
   Compressible Sugar, USP 86.0 mg.
   Calcium Stearate 4.0 mg.
2. LHRH Antagonist 10.0 mg.
   Compressible Sugar, USP 88.5 mg.
   Magnesium Stearate 1.5 mg.
3. LHRH Antagonist 5.0 mg.
   Mannitol, USP 83.5 mg.
   Magnesium Starch, USP 1.5 mg.
4. LHRH Antagonist 10.0 mg.
   Pregelatinized Starch, USP 10.0 mg.
   Lactose, USP 74.5 mg.
   Pregelatinized Starch, USP 15.0 mg.
   Magnesium Stearate, USP 1.5 mg.

Method A. LHRH Antagonist is dissolved in a sufficient quantity of water to form a wet granulation when mixed with the sugar portion of the excipients. After complete mixing the granulation is dried in a tray of fluid-bed dryer. The dry granulation is then screened to break up any large aggregates and then mixed with the remaining components. The granulation is then compressed on a standard tableting machine to the specific tablet weight.

Method B. In this manufacturing method, all formulations would include 0.01% gelatin, USP. The gelatin would be first dissolved in the aqueous granulation solvent followed by the LHRH analog. The remaining steps are as in (a) above.

EXAMPLE XXI

Long Acting intramuscular injectable formulation

Long Acting iM. Injectable-Sesame Oil Gel
LHRH Antagonist 10.0 mg.
Aluminum Monostearate, USP 20.0 mg.
Sesame oil g.s. ad 1.0 ml.

The aluminum monostearate is combined with the sesame oil and heated to 125° C. with stirring until a clear yellow solution forms. This mixture is then autoclaved for sterility and allowed to cool. The LHRH antagonist is then added aseptically with trituration. Particularly preferred LHRH antagonists are salts of low solubility, e.g., zinc salts, zinc tannate salts, pamoate salts, and the like. These exhibit exceptionally long duration of activity.

EXAMPLE XXII

Long Acting IM Injectable-Biodegradable Polymer Microcapsules

LHRH Antagonists 1%
25/75 glycolide/lactide copolymer (0.5 intrinsic viscosity) 99%
Microcapsules (0°–150°) of above formulation suspended in:
Dextrose 5.0%
CMC, sodium 0.5%
Benzyl alcohol 0.9%
Tween 80 0.1%
Water, purified q.s. 100.0%
25 mg. of microcapsules are suspended in 1.0 ml. of vehicle.

EXAMPLE XXIII

Aqueous Solution for Intramuscular Injection

LHRH Antagonist 500 mg.
Gelatin, nonantigenic 5 mg.
Water for injection g.s. ad 100 ml.

The gelatin and LHRH antagonist are dissolved in water for injection, then the solution is sterile filtered.

EXAMPLE XXV

Formulation for Rectal Administration

Suppository Vehicle for Rectal Administration

LHRH Antagonist 5.0 mg.
Witepsol H15 20.0 mg.

The LHRH antagonist is combined with the molten Witepsol H15, mixed with and poured into 2 gm. molds.

We claim:

1. A peptide selected from the group of peptides having the formula:

$$X-R^1-R^2-R^3-Ser-Tyr-R^6-Leu-Arg-Pro-R^{10}-NH_2$$

wherein
X is an acyl group derived from straight or branched chain aliphatic or alicyclic carboxylic acids having from 1 to 7 carbon atoms,
$R^1$ is D- or L-Pro, D- or L-$\Delta^3$-Pro, D-Phe, D-Phe(4-H1), D-Ser, D-Thr, D-Ala, D-Nal(1) or D-Nal (2),
$R^2$ is D-Phe or D-Phe(4-H1),
$R^3$ is D-Trp, D-Phe, D-Pal, D-Nal(1) or D-Nal (2),
$R^6$ is D-Cit, D-Hci, D-Cit(Q) or D-Hci(Q) and
$R^{10}$ is Gly or D-Ala,
where Q2 is lower alkyl of 1-3 carbon atoms and H1 is fluoro, chloro or bromo,
and the pharmaceutically acceptable acid addition salts thereof.

2. A peptide of claim 1 wherein
$R^1$ is D- or L-Pro, D-Phe, D-Phe(4-Cl), D-Nal (2),
$R^2$ is D-Phe(4-F) or D-Phe(4-Cl), and
$R^3$ is D-Trp.

3. A peptide selected from the group of peptides having the formula:

$$X-R^1-R^2-R^3-Ser(X^4)-Tyr(X^5)-R^{*6}(X^6)-Leu-Arg(X^8)-Pro-R^{10}-NH-X^{10}$$

wherein

X is an acyl group derived from straight or branched chain aliphatic or alicyclic carboxylic acids having from 1 to 7 carbon atoms, t-Boc or hydrogen, $X^4$ is hydrogen or a protecting group for the Ser hydroxyl group, $X^5$ is hydrogen or a protecting group for the Tyr phenolic hydroxyl group, $X^6$ is hydrogen or a protecting group for the Lys or Orn side chain amino group, $X^8$ is hydrogen or a protecting group for the Arg guanidino group, $X^{10}$ is hydrogen or a resin support containing benzhydryl or methylbenzhydryl groups, $R^1$ is D- or L-Pro, D- or L$\Delta^3$-Pro, D-Phe, D-Phe(4-H1), D-Ser, D-Thr, D-Ala, D-Nal(1) or D-Nal (2), $R^2$ is D-Phe or D-Phe(4-H1), $R^3$ is D-Trp, D-Phe, D-Pal, D-Nal(1) or D-Nal (2), $R^6$ is D-Lys or D-Orn and $R^{10}$ is Gly or D-Ala, where H1 is fluoro, chloro or bromo, provided that where X is t-Boc or hydrogen, $X^4$, $X^5$, $X^6$, and $X^8$ must be other than hydrogen.

4. A Peptide of claim 3 wherein
$X^4$ is hydrogen or 2,6-dichloro-benzyl,
$X^5$ is hydrogen or Z(2-Br) or 2,6-dichlorobenzyl,
$X^6$ is hydrogen or Z(2-Cl) and
$X^8$ is hydrogen, nitro, Tos, methyl-(t-butylbenzyl)sulfonyl or 4-methoxy-2,3,6-trimethyl benzylsulfonyl.

5. A Peptide of claim 4 wherein
$X^4$ and $X^5$ are hydrogen or benzyl,
$X^6$ is hydrogen or Z(2Cl), and
$X^8$ is hydrogen or Tos.

6. A peptide of claim 2 wherein X is acetyl.

7. A peptide of claim 6 wherein $R^1$ is Pro.

8. A peptide of claim 6 wherein $R^1$ is D-Nal(2).

9. A peptide of claim 6 wherein $R^1$ is D-Phe(4-Cl).

10. A peptide of claim 6 wherein $R^1$ is D-Phe.

11. A peptide of claim 7 wherein $R^6$ is D-Cit or D-Cit(Et).

12. A peptide of claim 7 wherein $R^6$ is D-Hci or D-Hci(Et).

13. A peptide of claim 8 wherein $R^6$ is D-Hci or D-Cit.

14. A peptide of claim 9 wherein $R^6$ is D-Hci or D-Cit.

15. A peptide of claim 10 wherein $R^6$ is D-Cit or D-Cit(Et).

16. A peptide of claim 10 wherein $R^6$ is D-Hci or D-Hci(Et).

17. A pharmaceutical composition for reducing the physiological availability of pituitary gonadotropins in a mammal which comprises a reductively effective amount of a compound of claim 1 and a pharmaceutically acceptable carrier.

18. A method of reducing the physiological availability of pituitary gonadotropins in mammals in need of such reduction which comprises administering thereto a reductively effective amount of a compound of claim 1.

19. A method of claim 18 wherein the amount is between 0.1 and 2.5 mg/kg body weight per day.

* * * * *

UNITED STATES PATENT AND TRADEMARK OFFICE
CERTIFICATE OF CORRECTION

PATENT NO. : 4,800,191
DATED : January 24, 1989
INVENTOR(S) : Andrew V. Schally, et al.

It is certified that error appears in the above-identified patent and that said Letters Patent is hereby corrected as shown below:

Column 2, line 24, delete "$R_3$", insert -- $R^2$ --.
line 25, delete "$R_6$", insert -- $R^3$ --.
line 27, delete "$R_{10}$", insert -- $R^6$ --.

Column 4,
line 9, delete "$R_3$", insert -- $R^2$ --.
line 10, delete "$R_6$", insert -- $R^3$ --.
line 11, delete "$R_{10}$", insert -- $R^6$ --.

Signed and Sealed this

Fourteenth Day of September, 1999

Attest:

Q. TODD DICKINSON

*Attesting Officer*  *Acting Commissioner of Patents and Trademarks*